United States Patent [19]
Szacon

[11] Patent Number: 5,271,500
[45] Date of Patent: Dec. 21, 1993

[54] SHARP MEDICAL UTENSIL CONTAINER

[75] Inventor: Joseph Szacon, Mt. Clemens, Mich.

[73] Assignee: Engineered Power Industries, Inc., Canton, Mich.

[21] Appl. No.: 791,471

[22] Filed: Nov. 8, 1991

[51] Int. Cl.⁵ .............................................. B65D 85/24
[52] U.S. Cl. .................................. 206/366; 220/4.28; 220/339; 220/6; 220/908
[58] Field of Search ............... 206/364, 365, 366, 369, 206/370; 220/4.28, 62, 908, 333, 334, 339, 6

[56] References Cited

U.S. PATENT DOCUMENTS

| | | |
|---|---|---|
| 2,962,155 | 11/1960 | Rusciano . |
| 2,971,688 | 2/1961 | Akers . |
| 2,990,059 | 6/1961 | Hitt . |
| 3,642,102 | 2/1972 | Furniss et al. ................. 220/339 X |
| 3,854,650 | 12/1974 | Hanave ............................. 220/334 X |
| 3,900,157 | 8/1975 | Roth .................................. 220/339 X |
| 3,900,550 | 8/1975 | Oliver et al. . |
| 3,933,296 | 1/1976 | Ruskin et al. .................... 220/339 X |
| 4,040,419 | 8/1977 | Goldman . |
| 4,106,621 | 8/1978 | Sorenson . |
| 4,121,755 | 10/1978 | Meseke et al. . |
| 4,143,695 | 3/1979 | Hoehn ................................. 220/339 |
| 4,235,346 | 11/1980 | Liggett ............................... 220/339 X |
| 4,315,592 | 2/1982 | Smith . |
| 4,328,904 | 5/1982 | Inverson . |
| 4,375,849 | 3/1983 | Hanifi . |
| 4,452,358 | 6/1984 | Simpson . |
| 4,520,926 | 6/1985 | Nelson . |
| 4,679,700 | 7/1987 | Tharrington et al. . |
| 4,722,472 | 2/1988 | Bruno . |
| 4,804,090 | 2/1989 | Schuh . |
| 4,826,073 | 5/1989 | Bruno . |
| 4,969,554 | 11/1990 | Sawaya . |
| 4,979,616 | 12/1990 | Clanton . |
| 4,982,843 | 1/1991 | Jones . |
| 4,986,438 | 1/1991 | Borst ................................... 220/339 X |
| 5,123,540 | 6/1992 | Karavias ............................ 220/339 X |

Primary Examiner—Steven N. Meyers
Assistant Examiner—Jacob K. Ackun, Jr.
Attorney, Agent, or Firm—Harness, Dickey & Pierce

[57] ABSTRACT

The present invention relates to a sharp utensil container and, more particularly, to a sharp medical utensil container. The container includes first and second top flaps which can be selectively rotated to provide an entrance to a containment area into which the utensil is deposited. The container also has a pair of side flaps which partially extend over the containment area against which the top flaps are biased to close the entrance. A key feature of the present invention are the upwardly projecting tab members which occur on the top surface of the top flaps which serve to limit the lateral movement of the utensil as it is being inserted into the container.

21 Claims, 2 Drawing Sheets

SHARP MEDICAL UTENSIL CONTAINER

BACKGROUND AND SUMMARY OF THE INVENTION

The present invention relates to a disposable sharp instrument container, and more particularly to a sharp instrument container for receiving potentially injurious or contaminated utensils such as syringes, hypodermic needles, scalpel blades and other utensils.

A need has developed for a container which can store devices such as syringes, sutures, hypodermic needles, scalpel blades and other utensils after use to eliminate the risks of exposing individuals to various diseases such as Hepatitis V or HIV, the virus which leads to Acquired Immune Deficiency Syndrome (AIDS). These and other diseases may be transmitted to individuals who are poked or cut by a contaminated sharp medical utensil. Due to the hectic conditions often present in hospitals and other medical facilities, used sharp medical utensils can often be found laying about in the present of patients, doctors, nurses and other medical personnel. By providing a transportable sharp medical container, these used sharp medical utensils can be deposited immediately after use to reduce the likelihood of exposure to patients, doctors, nurses and other medical personnel.

Many containers having one or more flaps which cover the containment area are known in the art. Predominately, problems occur with these containers wherein the soiled sharp medical utensils gets stuck between the flaps during insertion into the container. This creates a risk of injury to the medical personnel while attempting to store the used sharp medical utensil.

In addition, the presently known sharp medical utensil containers generally are not provided with sufficient means of limiting lateral movement of the sharp medical utensil as it is being inserted into the sharp medical utensil container.

It is therefore a primary object of the present invention to provide a sharp medical utensil container having flaps which can be flexed easily to provide access to the containment area and which minimizes the possibility of the sharp medical utensil getting stuck between the flaps as it is being inserted into the container.

It is a further object of the present invention to provide a container which has guide means for limiting lateral movement of the sharp medical utensil as it is being inserted into the sharp medical utensil container.

It is a further object of the present invention to provide a container which is reusable after being sterilized.

Other advantages and features will become apparent from the following specification taken in connection with the accompanying drawings.

BRIEF DESCRIPTION OF PREFERRED EMBODIMENTS

DETAILED DESCRIPTION OF THE PREFERRED EMBODIMENT

Figure 1:
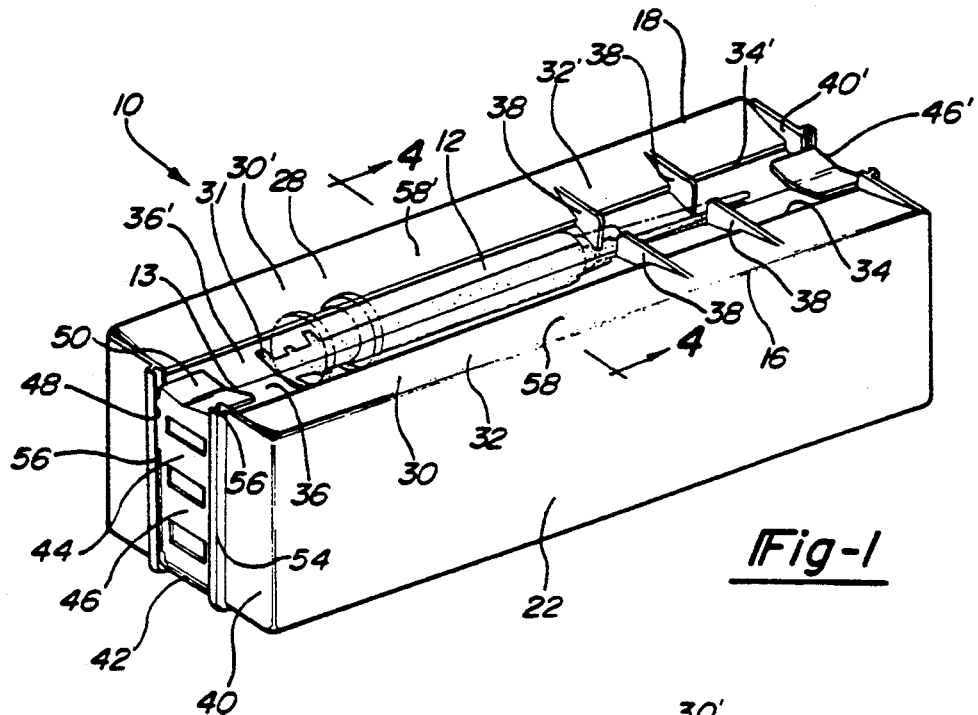
FIG. 1 is a perspective view of the present invention.

Referring to FIG. 1, a cross-sectional view of the container 10 embodied by the present invention is shown. Container 10 is designed to receive sharp utensils, and more particularly, sharp medical utensils such as syringes, hypodermic needles, scalpels and other sharp medical utensils. For purposes of demonstration, a syringe 12 will be utilized to explain the use of the present invention. Container 10 includes a front wall 22, a back wall 24, a bottom 26, a top 28 defined by two symmetrical opposable flaps 30 and 30' and two side walls 40 and 40' having projecting flaps 46 and 46'. The top flaps 30 and 30' include two planar portions separated by a step. The first flap 30 has a first planar portion 32 which is attached to the front wall 22 by living hinge 16. A relatively horizontal transitional step 34 connects a second planar portion 36 to the first planar portion 32. Likewise, the second top flap 30' has a first planar portion 32' which is attached to the back wall 24 by a living hinge 18. The second top flap 30' also has a relatively horizontal transitional step 34' which connects a second planar portion 36' to the first planar portion 32'. When the container 10 is being assembled, both the first and second top flaps 30 and 30' are folded inward toward the containment area 14 such that when the top flaps abut, the entrance 13 to the containment area 14 is substantially closed. Both top flaps 30 and 30' are provided with tabs 38 which project upwardly from the top surfaces 58 and 58' of the flaps 30 and 30' to align the syringe 12 prior to insertion of the syringe 12 into the containment area 14.

Figure 2:
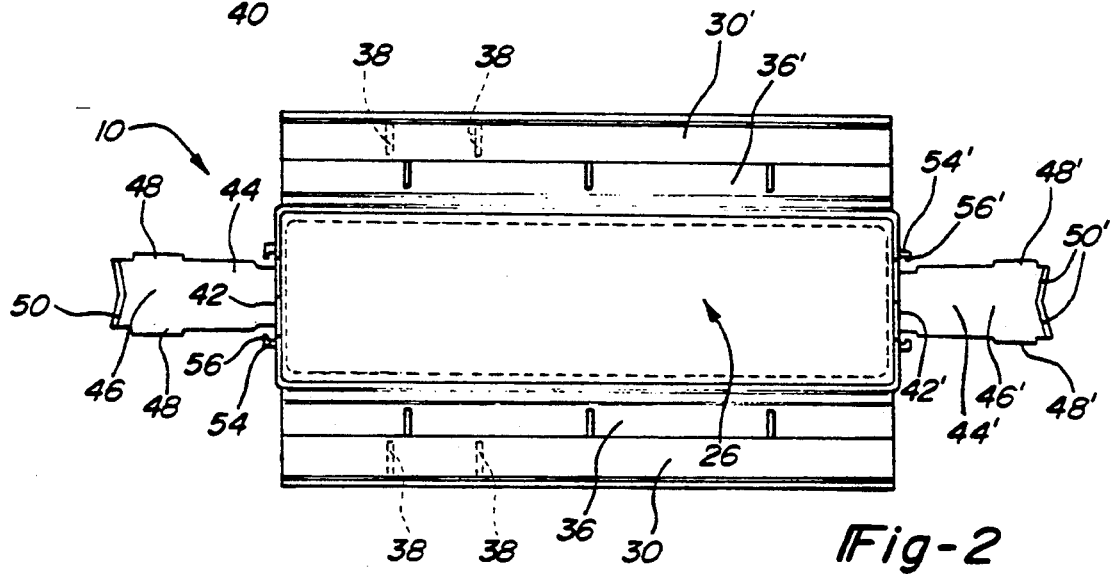
FIG. 2 is a top view showing the side flaps in a nonoperative position.

Referring to FIG. 2, a top view showing the side flaps in a nonoperative position is provided. A first side wall 40 includes a projecting flap 44 connected near the base of the side wall 40 via a living hinge 42. The side wall 44 has a first relatively flat section 46 which has stops 48 projecting therefrom and a substantially V-shaped second section 50 which extends upwardly from the first section 46 when the side flap 44 is in a nonoperative position. The side wall 40 is also provided with a pair of opposing flanges 54 which project out from the side wall 40. Each flange 54 has an incurved lip 56 which extends in the direction of the opposing flange. Likewise, the second side wall 40' includes a projecting flap 44' connected near the base of the side wall 40' by a living hinge 42'. The flap 44' has a first relatively flat section 46' with projecting stops 48' and a second substantially V-shaped second section 50' which extends upwardly from the first section 46' when the side flap 44' is in a nonoperative position. The side wall 40' is also provided with a pair of opposing flanges 54' which project out from the side wall 40'. Each flange 54' has an incurved lip 56 which extends in the direction of the opposing flange.

Figure 6:
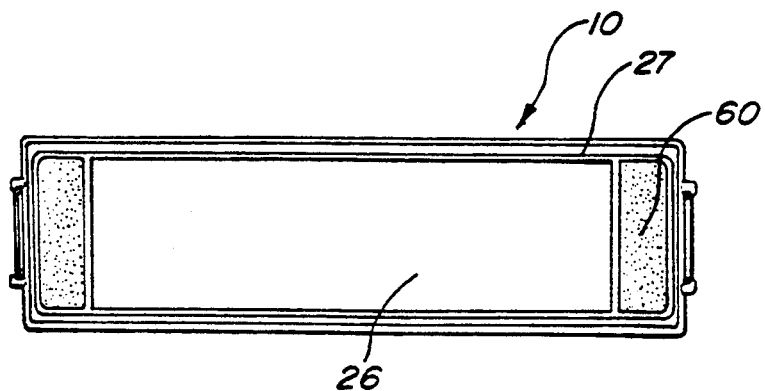
FIG. 6 is a bottom view of the present invention incorporating stabilizing pads.

Referring to FIG. 6, a bottom view of the present invention is shown to incorporate stabilizing pads which limit the undesired movement of the container 10. A rim 27 is provided on the bottom substantially outlining the bottom of the container 10. Stabilizing pads 60 may be attached anywhere upon the container bottom 26 within the projecting rim area. Preferably, the stabilizing pad 60, having a similar thickness and will be attached at each end of the container as shown in FIG. 6 so that the container 10 is balanced.

Figure 3:
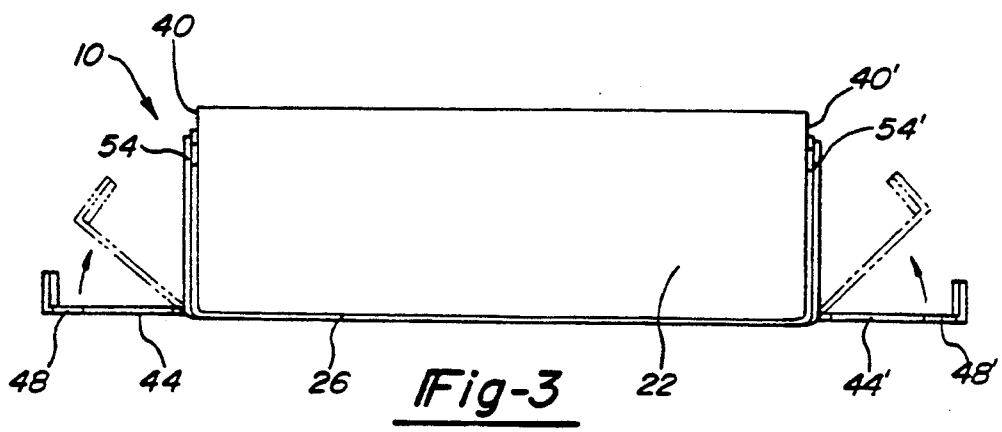
FIG. 3 is a side view showing the side flaps being rotated upwardly from a nonoperative position.
Figure 4:
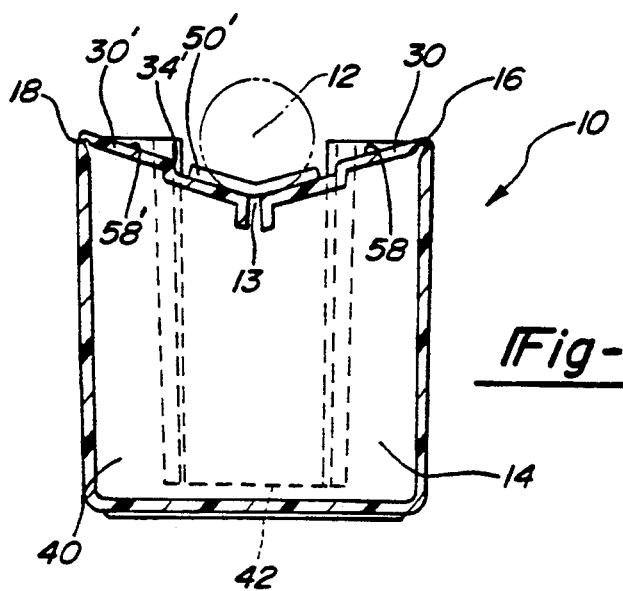
FIG. 4 is a cross-sectional view along line 4—4 as shown in FIG. 1.
Figure 5:
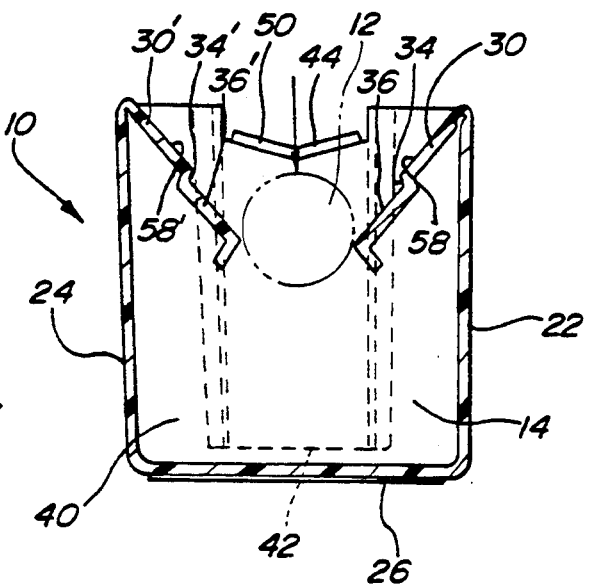
FIG. 5 is a view similar to FIG. 4 showing a medical utensil being inserted into the containment area.

Referring to FIGS. 3, 4 and 5, a method of storing a sharp medical utensil such as a syringe 12 is shown. After the top flaps 30 and 30' have been folded into a containment area 14, the side flaps 44 and 44' are rotated upward as shown in FIG. 3 to engage the side wall flanges 54 and 54'. Stops 48 and 48' snap into the side wall flanges so that the flaps 44 and 44' are locked contiguously against side walls 40 and 40', respectively. It is contemplated that once the side flaps 44 and 44' are snapped under flanges 54 and 54', respectively, the side flaps 44 and 44' and flanges 54 and 54' can be permanently bonded together by adhesives or by sonic welding, if desired. The flange lips 56 overlap the stops 48 and 48' so that the flaps 44 and 44' remain contiguously against the side walls 40 and 40'. When the flaps 44 and 44' are secured in the operative position by the flanges 54 and 54', the substantially V-shaped sections 50 and 50' partially overlap the top flaps 30 and 30' and the containment area 14. Living hinges 16 and 18 cause the top flaps 30 and 30', respectively, to flex upwardly. As a result, the top flaps 30 and 30' are biased against the bottom portion of the V-shaped side flap second sections 50 and 50'. The V-shaped side flap sections 50 and 50' cause the top flaps 30 and 30' to be flexed progressively downward toward the entrance 13 beginning at the hinges 16 and 18 of the container 10 forming a longitudinally depression at the entrance 13.

The syringe 12 is placed upon the top flaps 30 and 30' by hand or by an instrument such as forceps. An embossed syringe outline 31 is provided on the top surfaces 58 and 58' of the top flaps to assist the user in aligning the syringe upon the top flaps along the longitudinal depression. The needle portion of syringe 12 is positioned between the tabs 38 to align and limit lateral movement of the syringe 12. Steps 34 and 34' also assist in limiting lateral movement of the syringe once placed within the depression. Once the syringe 12 is properly positioned upon the top flaps 30 and 30', the syringe 12 is pushed downwardly upon the top flaps 30 and 30' causing them to rotate about the living hinges 16 and 18 thereby widening the entrance 13 to the containment area 14. With continuous downward pressure, the entrance 13 is sufficiently opened so that the syringe 12 drops into the containment area 14. After the syringe drops into the containment area 14, the top flaps 30 and 30' spring upwardly to be biased against the side flap second sections 50 and 50', respectively, thereby closing entrance 13 to contain the soiled syringe 12.

The container 10 of the present invention allows for the containment of a plurality of various sized sharp medical utensils. Preferably the container is made of a recyclable plastic such as polypropylene which is transparent in nature. Dyes can be added to the polypropylene prior to molding the container 10 if desired. For example, the present invention can be provided with an overall red color to comply with state and federal regulations regarding the identification of biohazardous containers. It is further contemplated that the container 10 may be reused after the utensils have been carefully removed and the container has been sterilized. While the present invention has been specifically designed to retain certain sharp medical utensils, it will be understood that other items such as bullets, knives, and other articles of evidence may be stored in the container.

While it will be apparent that the preferred embodiments of the invention disclosed are well calculated to provide the advantages stated above, it will be appreciated that the invention is susceptible to modification, variation and change without departing from the proper scope and fair meaning of the subjoined claims.

What is claimed:

1. A container for receiving a utensil having a containment area, said container comprising:
    a bottom and first and second sidewalls defining said containment area.
    a top including first and second opposable flaps operable to define an entrance into said containment area for said utensil, said first and second flaps being biased together to close said entrance; and
    wherein at least one of said side walls includes a third flap having a first section and a second section angled away from said first section, said third flap capable of being moved to a first position in which said first section is substantially coplanar with said one of said side walls and to a second position in which said first section is not substantially coplanar with said one of said side walls, said second of said third flap being operable to limit movement of said first and second flaps in an upwardly direction when said first section of said third flap is in said first position;
    whereby said utensil may be retained within said container by inserting said utensil into said containment area.

2. The container as claimed in claim 1, wherein said first and second flaps are selectively flexible about living hinges.

3. The container as claimed in claim 1, wherein said first and second flaps include at least one tab projecting upwardly from a top surface of said top, said at least one tab being operable to align said utensil upon said first and second flaps.

4. The container as claimed in claim 1, wherein said first and second flaps are provided with means for depicting the insertion of said utensil into said containment area.

5. The container as claimed in claim 1, wherein said means for depicting the insertion of said utensil into said containment area further comprises an embossed utensil outline.

6. The container as claimed in claim 1, wherein said first and second flaps include a first relatively planar portion and a second relatively planar portion, said second relatively planar portion being located below said first planar portion, said first and second relatively planar portions being separated by a step which is operable to limit lateral movement of said utensil when said utensil is disposed on said second relatively planar portion.

7. The container as claimed in claim 1, said second section being disposed relatively perpendicular to said first section, said second section of said third flap being substantially V-shaped in cross-section wherein said second section of said third flap is operable to position said first and second flaps downwardly thereby forming a centrally located longitudinal depression.

8. The container as claimed in claim 7, wherein said first section of said third flap is removably secured by at least one projecting flange.

9. The container as claimed in claim 8, wherein said first section of said third flap includes at least one stop projecting from a side edge thereof, said at least one stop being operable to be snapped under said projecting flange to removably secure said third flap substantially against said at least one of said side walls.

10. The container as claimed in claim 1, wherein said third flap is further secured to said at least one of said side walls by a living hinge.

11. The container as claimed in claim 1, said bottom including means for limiting movement of said container.

12. The container as claimed in claim 11, wherein said means for limiting the movement of said container further comprises at least one stabilizing pad.

13. The container as claimed in claim 1, wherein a sterilizing material is disposed within said container.

14. A container for receiving a utensil having a containment area, said container comprising:
   a bottom and at least one side wall defining said containment area,
   a top portion having first and second flaps operable to define an entrance into said containment area for said utensil, said first and second flaps being biased to close said entrance; and
   said at least one side wall having a selectively rotatable third flap, said third flap having a first section and a second section angled away from said first section, said second section of said third flap being operable to limit movement of said first and second flaps in an upwardly direction when said first section of said third flap is rotated so as to be in substantially planar relationship with said at least one side wall and is retained in said relationship by means on said at least one side wall for removably securing said third flap.

15. A container as claimed in claim 14, wherein said first and second flaps include means for limiting lateral movement of said utensil.

16. A container as claimed in claim 15, wherein said means for limiting lateral movement of said utensil include tab members projecting upwardly from a top surface of said first and second flaps.

17. An container as claimed in claim 16, wherein said means for limiting lateral movement of said utensil further comprise providing said first and second flaps with a first relatively planar portion and a second relatively planar portion, said second relatively planar portion being located below said first planar portion, wherein said first and second relatively planar portions are separated by a step, whereby said step is operable to limit lateral movement of said utensil when said utensil is disposed on said second relatively planar portion.

18. A container for receiving a utensil as claimed in claim 14, wherein said means for removably securing said third flap includes at least one incurved flange member projecting from said side wall.

19. A container for receiving a utensil as claimed in claim 18, wherein said first section of said third flap includes at least one stop projecting from a side edge thereof, said stop being operable to snap under said at least one incurved flange member to removably secure said third flap.

20. A container as claimed in claim 19, wherein said second section of said third flap is substantially V-shaped in cross-section, said second section being operable to dispose said first and second flaps downwardly to form a centrally located longitudinal depression.

21. A container as claimed in claim 20, wherein said third flap is further secured to said side wall by a living hinge.

* * * * *